United States Patent [19]

Tsuchiya

[11] Patent Number: 5,747,277
[45] Date of Patent: May 5, 1998

[54] PROCESS FOR DETECTING MICROORGANISMS

[75] Inventor: Masakazu Tsuchiya, Ako, Japan

[73] Assignee: Wako Pure Chemical Industries, Ltd., Osaka, Japan

[21] Appl. No.: 685,546

[22] Filed: Jul. 24, 1996

[30] Foreign Application Priority Data

Jul. 31, 1995 [JP] Japan ................... 7-214200

[51] Int. Cl.$^6$ ............... C12Q 1/04; C12Q 1/54; C12Q 1/26; C12Q 1/00
[52] U.S. Cl. ............... 435/34; 435/14; 435/25; 435/4; 435/15; 435/18; 435/16; 530/300
[58] Field of Search ................. 435/34, 14, 25, 435/4, 15, 16, 18; 530/300

[56] References Cited

U.S. PATENT DOCUMENTS 4,970,152  11/1990  Ashia et al. ................. 435/25
5,585,248  12/1996  Ashida et al. ................. 435/25

OTHER PUBLICATIONS

Yoshida et al; Biochemical and Biophysical Research Communications; vol. 141 No. 3, pp. 1177–1184, 1986. Month Not Available.

Tsuchiya et al; English Abstract. (Measurement of Endotoxin & Peptidoglycan for Detection of Bacteria); Endotokishin Shinpojumn Koen Kirokushu, 7th (1994). Month Not Available.

*Primary Examiner*—Louise Leary
*Attorney, Agent, or Firm*—Armstrong, Westerman, Hattori, McLeland & Naughton

[57] ABSTRACT

Microorganisms in a sample can be detected easily and rapidly with high precision by a process which comprises filtering the sample through a filter, washing the filter, reacting the residue on the filter with an insect hemolymph containing inactive type factors of the pro-phenol oxidase cascade, and detecting the microorganisms in the sample on the basis of the color change thus caused.

4 Claims, 4 Drawing Sheets

PROCESS FOR DETECTING MICROORGANISMS

BACKGROUND OF THE INVENTION

This invention relates to a process for detecting microorganisms, which is utilized, for example, for quality control of washing water for semiconductors, diagnoses of infectious diseases, detection of environmental microorganisms, inspection for microorganisms in foods, etc.

Microorganisms are detected for various purposes, for example, quality control of washing water for semiconductors, diagnoses of infectious diseases, detection of environmental microorganisms, and inspection for microorganisms in foods.

As a method for detecting microorganisms, there can be exemplified ① culturing method comprising adding a sample directly to a medium and counting the thus formed colonies, ② total cell number counting method comprising collecting cells in a sample on a filter by filtering the sample, followed by fixing, fluorescent staining, and cell counting by microscopic observation, ③ polymerase chain reaction (PCR) method comprising investigating the existence of a nucleic acid (polynucleotide) chain characteristic of a strain, ④ flow cytometry method comprising fluorescent labeling of cells, followed by detection, ⑤ ATP detection method comprising counting cells by detecting adenosine 5'-triphosphate (ATP) in the cells. All of these methods involve some problem and cannot be methods which permit easy and rapid detection.

For example, the culture method is disadvantageous in that it does not permit rapid detection because culturing usually requires 24 hours or more (1 week or more for the detection of Eumycetes in some cases). It is disadvantageous also in that since some bacteria cannot be cultured by a conventional method, microorganisms in a sample are overlooked in some cases. The total cell number counting method is disadvantageous in that expensive equipments such as a fluorescence microscope, image analyzer, etc. are necessary for cell counting. The PCR method is disadvantageous in that it is difficult to count the total number of microorganism cells. The flow cytometry method is disadvantageous, for example, in that the limit of detection of microorganisms is low and that the precision of measurement is lowered by noises due to a reagent for fixing (e.g. formalin). The ATP detection method is disadvantageous in that an expensive measuring apparatus is necessary for the detection.

For solving such problems, there is investigated a method which comprises mixing a sample to be tested for microorganisms, with an insect body fluid containing inactive type factors of the pro-phenol oxidase cascade (the insect body fluid is hereinafter abbreviated as "PPO reagent") to react them, observing, for example, the degree of coloration due to at least one microorganism cell wall component such as (1→3)-β-D-glucan (hereinafter abbreviated as "β-glucan") or peptidoglycan, and detecting the microorganisms on the basis of the observation result. This method, however, is not preferable because it involves, for example, the following problems. Since the sample is mixed directly with the PPO reagent in this method, the detection tends to be affected by, for instance, the salt concentration in the sample. In detail, when the salt concentration is high, the detection sensitivity is lowered, so that much labor is required for determining the detection conditions. For detecting microorganisms in a sample having a high salt concentration, it is usually unavoidable that the test for the microorganisms is conducted on the sample properly diluted. Therefore, the detection sensitivity and the precision of measurement are lowered. In the case of a sample contaminated with β-glucan not derived from microorganisms, the detection result may be false-positive.

SUMMARY OF THE INVENTION

In view of such circumstances, a problem to be solved by the present invention is to provide a process which permits easy, rapid, and high-precision detection of microorganisms in various samples.

The present invention provides a process for detecting microorganisms which comprises filtering a sample through a filter, washing the filter, reacting the residue on the filter with an insect body fluid containing inactive type factors of the pro-phenol oxidase cascade, and detecting microorganisms in the sample on the basis of the color change thus caused.

DESCRIPTION OF THE PREFERRED EMBODIMENTS

The process for detecting microorganisms of the present invention comprises filtering a sample through a filter, washing the filter, reacting the residue on the filter with a PPO reagent, and detecting microorganisms in the sample on the basis of the color change thus caused.

The present invention has been accomplished on the basis of, for example, the following findings made by the present inventors in the course of earnest investigation for finding a process which permits easy, rapid, and high-precision detection of microorganisms in various samples by use of a PPO reagent. When a sample is filtered through a filter having a suitable pore size and the filter is washed and then subjected to reaction with a PPO reagent, the advantages described below can be obtained. (1) One or more objective microorganisms can be detected easily and rapidly with high precision without the following problems in employment of a PPO reagent: the detection tends to be affected by the salt concentration in a sample, and when the salt concentration is high, the detection sensitivity is lowered, so that much labor is required for determining the detection conditions; in such a case, since it is unavoidable that the test for microorganism is conducted on the sample suitably diluted, the detection sensitivity and the precision of measurement are lowered; in the case of a sample contaminated with β-glucan not derived from microorganism, the detection result may be false-positive. (2) The sample is concentrated by the filtration through the filter, so that the detection sensitivity is enhanced.

A sample to which the detection process of the present invention can be applied is not particularly limited so long as the detection of the presence of microorganisms in the sample is necessary. The sample includes, for example, washing water for semiconductors, body fluids (e.g. blood, plasma, serum and cerebrospinal fluid), urine, tap water, factory wastes, foods, drinks, solutions after washing an instrument such as a hemodialyzer, a medical instrument, etc.

Although the filter used in the present invention is not particularly limited so long as it has a suitable pore size and does not react with the PPO reagent (or reacts therewith only to such an extent that the detection of the microorganisms is not hindered). Preferable specific examples of the filter are sheet-like (film-like) filters which are prepared from a material such as a poly(vinylidene fluoride), polysulfone, polytetrafluoroethylene (PTFE), poly(vinylpyrrolidone) (PVP), polyamide, nylon, or a cellulose derivative (e.g. cellulose acetate, cellulose nitrate or a mixture thereof), and permits easy judgement of a coloration caused by the reaction of β-glucan and/or peptidoglycan with the PPO reagent. A filter made of the cellulose derivative which is generally tend to be contaminated with β-glucan, and thus when such a filter as above is used, check has to be made as to whether it is contaminated or not. If contaminated, it is desirable to use a conventional means for removing the contamination.

As the filter used in the present invention, a commercially available one may be used as it is. Specific examples of the commercially available filter are Durapore (a poly (vinylidene fluoride) filter, mfd. by Japan Millipore Ltd.), HT Tuffryn (a polysulfone filter, mfd. by Gelman Sciences Inc.), Millex (a polytetrafluoroethylene filter, mfd. by Japan Millipore Ltd.), Isopore (a poly(vinylpyrrolidone) filter, mfd. by Japan Millipore Ltd.), a polyamide filter (available from Sartorius AG), a nylon filter (available from Corning Inc.), cellulose acetate filter and a cellulose nitrate filter (available from Iwaki Glass Co., Ltd.), and MF-Millipore, a cellulose filter (available from Japan Millipore Ltd.).

In the present invention, the kinds of the microorganisms to be measured can be specified to a certain extent by properly choosing the pore size of the filter used. For example, when the detection of bacteria and Eumycetes is desired, a filter having a pore size of 0.2 μm or 0.45 μm is preferable. When the detection of Eumycetes such as yeasts and molds is desired, a filter having a pore size of 1.2 μm to 3 μm is preferable. When the detection of molds is desired, a filter having a pore size of 5 μm or more is preferable. In a case where a sample contains plural kinds of microorganisms including bacteria, the sample is, for example, filtered through a filter having a pore size of 1.2 μm to 3 μm, the filtrate is filtered through a filter having a pore size of 0.2 μm or 0.45 μm, and then the latter filter is subjected to the detection of the present invention, whereby only the bacteria among those microorganisms can be detected.

As the filter used in the present invention, either of the following types may be used: (1) a product composed of a sheet-like filter and a holder which are separate from each other and thus can be individually sterilized, and (2) an integral-type, disposable and sterilized product. There may also be used a microtiter plate equipped with a filter (e.g. Multiscreen GV Filter Plate, mfd. by Japan Millipore Ltd.).

When such a filter is contaminated with peptidoglycan or β-glucan, it is desirable to use a conventional means for removing the contamination.

As the PPO reagent used in the present invention, any PPO reagent may be used so long as it is obtained from the body fluid of an insect, contains inactive type factors of the pro-phenol oxidase cascade and can react with at least one of β-glucan and peptidoglycan which are present in the cell walls of microorganisms, to activate phenol oxidase. Since the PPO reagent is blakened by the reaction with β-glucan and/or peptidoglycan which are present in the cell walls of microorganisms, it is used as it is for the purpose of the present invention, though it may be used after being incorporated with a so-called synthetic substrate, i.e., a substance which is a substrate for an enzyme activable by the reaction of the PPO reagent with β-glucan and/or peptidoglycan and produces a suitable coloring matter or the like including fluorescent ones, owing to the action of the enzyme.

The PPO reagent is usually prepared from the body fluid of an insect by a conventional method, and the reagent can be prepared by proper combination of inactive type factors of the pro-phenol oxidase cascade which are prepared by genetic recombination.

Although the insect from which the body fluid is collected is not particularly limited, it is preferably as large as possible and can be reared by an established method. The insect includes, for example, Lepidoptera order such as *Manduca serta, Gelleria melonella, Hyalphoma ceropia, Bombyx mori* (silkworm moth), etc.; Diptera order such as *Sarcophaga peregria, musca*, etc.; Orthoptera order such as *Locusta, migratoria Teleogryllus*, etc.; and Coleoptera order such as Cerambyx, etc. The insect is not limited to them. As the body fluid, hemolymph collected from the body cavity is most easily available and thus can usually be used.

As a method for collecting the body fluid from the above-exemplified insect, there can be exemplified a method of placing the insect on ice to stop its moving, injecting the body cavity with physiological saline containing sucrose containing a cane factor including a high-molecular weight substance comprising glucose, amino acid and other components which are obtained from sugar cane, as an impurity or physiological saline containing the cane factor itself, allowing the insect to stand for a while, and then collecting hemolymph from the body cavity. The hemolymph thus obtained is centrifuged to be freed of hemocytes, and then dialyzed, whereby there is obtained plasma which can be used as the PPO reagent according to the present invention. In this plasma, there coexist a substance capable of reacting specifically with β-glucan to exhibit an enzyme activity or induce the exhibition and a substance capable of reacting specifically with peptidoglycan to exhibit an enzyme activity or induce this exhibition. Therefore, when the plasma is used as the PPO reagent, it becomes possible to detect all of microorganisms containing β-glucan or peptidoglycan as a cell wall component. As such a reagent, there can be used a commercially available one (e.g. an SLP™ reagent set, available from Wako Pure Chemical Industries, Ltd.).

By properly treating the above-mentioned insect plasma, there can also be obtained a PPO reagent which reacts with β-glucan but not with peptidoglycan and a PPO reagent which reacts with peptidoglycan but not with β-glucan. Namely, an example of method for preparing the PPO reagent which permits specific detection of β-glucan is disclosed in JP-A 63-141598 (U.S. Pat. No. 4,970,152), and an example of method for preparing the PPO reagent which permits specific detection of peptidoglycan is disclosed in JP-A 63-141599 (U.S. Pat. No. 4,970,152).

In the following, further explanation is given on these methods.

In the plasma obtained in the manner described above, there coexist a substance which does not react with endotoxin but reacts specifically with β-glucan to exhibit an enzyme activity or induce the exhibition, and a substance which reacts specifically with peptidoglycan to exhibit an enzyme activity or induce this exhibition. To obtain the PPO reagent which permits specific detection of β-glucan, it is sufficient that the substance capable of reacting with peptidoglycan to exhibit an enzyme activity or induce the exhibition is removed from the aforesaid plasma. To obtain the PPO reagent which permits specific detection of peptidoglycan, it is sufficient that the substance capable of reacting with β-glucan to exhibit an enzyme activity or induce the exhibition is removed from the aforesaid plasma. As a method for removing from the aforesaid plasma the substance capable of reacting with peptidoglycan to exhibit an enzyme activity or induce the exhibition, or the substance capable of reacting with β-glucan to exhibit an enzyme activity or induce this exhibition, there can be exemplified all of separation and purification methods generally employed in the field of biochemistry. The substance capable of reacting with peptidoglycan to exhibit an enzyme activity or induce the exhibition can be removed very easily and efficiently by an affinity chromatography using a carrier having peptidoglycan bound thereto. The substance capable of reacting with β-glucan to exhibit an enzyme activity or induce this exhibition can be removed very easily and efficiently by an affinity chromatography using a carrier having β-glucan bound thereto.

The process of the present invention is actually practiced, for example, as follows.

First, a proper amount of a sample is filtered through such a suitable filter as is described above, to capture microorganisms including bacteria and Eumycetes (e.g. yeasts and molds) on the filter. Then, the filter is washed with a suitable washing solution to remove substances present in the sample except for the microorganisms. A proper volume of such a PPO reagent as is described above is dropped on the thus treated filter to allow the reaction to take place under definite conditions, for example, at 0°–50° C., preferably 20°–40° C., after which the color change of the filter is observed with the lapse of time. The presence of the microorganisms in the sample can be detected or their concentration in the sample can be determined on the basis of the difference between the color change caused in that case and that caused in each of a negative control test which is carried out with the same reagent by the same procedure as above except for using, as a sample, water, a buffer solution or the like, which is free from β-glucan and peptidoglycan, and a positive control test which is carried out with the same reagent by the same procedure as above except for using a sample solution containing a suitable concentration of microorganisms. In the above measurement, the semiquantitative determination of the microorganism concentration can be made possible by varying the positive control test.

In the above procedure, the following is also possible: a large number of samples are filtered using as a filter a filter-equipped microtiter plate (e.g. Multiscreen GV Filter Plate, mfd. by Japan Millipore Ltd.), and the filter is washed and then subjected to reaction with a PPO reagent, after which the color change of the filter is observed by means of a microtiter plate reader, and the presence of microorganisms in each sample is detected or their concentration in each sample is determined on the basis of the observation results. When the microorganisms are detected by such a method, an objective detection can be rapidly carried out in a large number of samples.

Moreover, since the above-mentioned detection is carried out by filtering a sample through a filter, washing the filter, and then subjecting the filter to reaction with a PPO reagent, there is almost no possibility that salts, water-soluble β-glucan and the like in the sample may affect the detection.

The washing solution used in the above-mentioned procedure is not particularly limited so long as it is not contaminated with β-glucan and peptidoglycan and does not deteriorate the performance characteristics of the filter. Preferable examples of the washing solution are water and solutions with a pH of 6 to 8 containing 10 to 150 mM, preferably 20 to 40 mM of a buffer (e.g. Good's buffer or phosphate buffer) or a salt (e.g. NaCl).

It is also possible to wash away water-insoluble β-glucan by using an alkali solution (10 mM to 4M, preferably 50 mM to 1M) as the washing solution. Therefore, in a sample which is expected to contain water-insoluble β-glucan, peptidoglycan from bacteria contained therein can be specifically detected by using a process for washing the filter with such a washing solution and then optionally such an ordinary washing solution as is described above.

In the detection of bacteria or Eumycetes in a sample containing a lipid (e.g. cosmetic cream, cream for foodstuff, etc.) or a sample containing an organic solvent, the influence of these substances present in the samples can be removed by washing the filter by using a suitable organic solvent as a washing solution, and then washing the filter with such an ordinary washing solution as is described above.

The present invention is illustrated below in further detail with reference to Examples and Comparative Examples, which are not by way of limitation but by way of illustration.

EXAMPLE 1

(1) Reagents and Instrument

PPO Reagent

There was used a solution prepared by dissolving a commercially available PPO reagent derived from silkworm hemolymph (SLP™ reagent, available from Wako Pure Chemical Industries, Ltd.; for 3 ml) in 6 ml of a solvent attached to SLP™ reagent kit (available from Wako Pure Chemical Industries, Ltd.).

Filter

Millex 4 mm GV (mfd. by Japan Millipore Ltd.) was used.

Water and Washing Solution

Water for injection mfd. by Otsuka Pharmaceutical Co., Ltd. was used.

3% Aqueous Sodium Chloride Solution

There was used a solution prepared by dissolving sodium chloride (mfd. by Wako Pure Chemical Industries, Ltd.; special grade) heat-treated at 250° C. for 2 hours, in the water for injection to a concentration of 3%.

(2) Samples

As samples, there were used suspensions prepared by suspending a lactic acid bacterium (*Lactobacillus delbrueckii*) or *E. coli* in an amount of $10^3$, $10^4$ or $10^5$ cells/ml in water for injection or a 3% aqueous sodium chloride solution.

(3) Detecting Procedure

The filter was washed with 2 ml of washing solution and then 1 ml of each of the predetermined samples was filtered through the washed filter. This filter was washed with 2 ml of washing solution, after which 0.01 ml of the PPO reagent was dropped thereon and the degree of coloring of the filter was visually observed.

(4) Results

Figure 1:
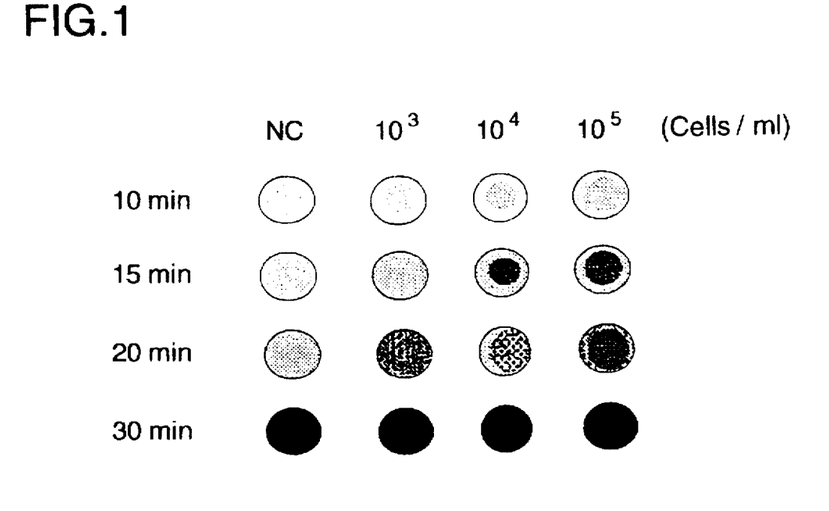
FIG. 1 shows the results of detection of a *Lactobacillus delbryckii* obtained in Example 1.
Figure 2:
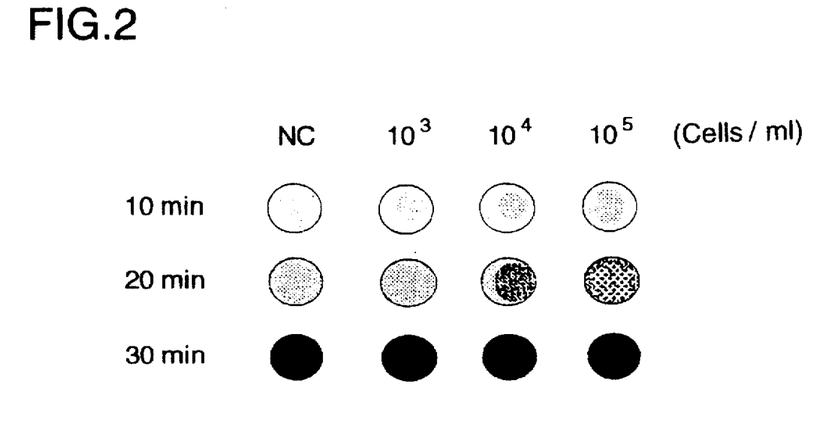
FIG. 2 shows the results of detection of *Escherichia coli* obtained in Example 1.

FIG. 1 shows the results obtained by using the *L. delbrueckii* suspensions having various concentrations prepared by use of water as samples. FIG. 2 shows the results obtained by using the *E. coli* suspensions having various concentrations prepared by use of water for injection as samples. Each of FIGS. 1 and 2 also shows results of a negative control test (NC) carried out for comparison by using, as a sample, the same water as used for preparing the various samples.

From FIGS. 1 and 2, it can be seen that the filter having cells retained thereon by the filtration shows clearly rapider coloration than does the filter treated by the negative control test (NC), and makes it possible to judge whether the reaction is positive or negative, 10 to 20 minutes after the initiation of the reaction. It can also be seen that *L. delbrueckii* can be detected even at a density of $10^3$ cells/ml and *E. coli* even at a density of $10^4$ cells/ml.

When the samples prepared by use of a 3% aqueous sodium chloride solution were used, the same results as above were obtained.

Comparative Example 1

Detection of microorganisms by a known method.
(1) Reagents and Instrument
PPO Reagent
The same as used in Example 1.
Water
The same as used in Example 1.
3% Aqueous Sodium Chloride Solution
The same as used in Example 1.
Measuring Apparatus
Toxinometer ET-301 (mfd. by Wako Pure Chemical Industries, Ltd.) was used.
(2) Samples
The same as used in Example 1.
(3) Detecting Procedure After 0.1 ml of the PPO reagent and 0.1 ml of a sample containing *L. delbruekii* or *E. coli* at a density of $10^4$ cells/ml were mixed and stirred, a Tg value (a time required for the amount of transmitted light to reach a predetermined definite value) was measured by means of a Toxinometer ET-301.
(4) Results When each of an *L. delbrueckii* suspension and an *E. coli* suspension which had been prepared by use of water was used as a sample, a Tg value for *L. delbrueckii* was 32.4 minutes and a Tg value for *E. coli* 59.4 minutes. Therefore, it can be seen that in the case of these samples, the reaction can be judged positive within a measurement time of 90 minutes. On the other hand, when each of an *L. delbrueckii* suspension and an *E. coli* suspension which had been prepared by use of a 3% aqueous sodium chloride solution was used as a sample, no Tg value could be obtained for either *L. delbrueckii* or *E. coli* within a measurement time of 90 minutes. Therefore, in the case of these samples, the reaction was not judged positive.

When the same measurement as above was carried out as a negative control test by using, as a sample, each of the same water for injection and 3% aqueous sodium chloride solution as used for preparing the samples, no Tg value could be obtained, namely the reaction was not judged positive, in either case.

From the results of Example 1 and Comparative Example 1, it can be seen that the application of the process of the present invention permits detection of microorganisms in a solution with a high salt concentration which cannot be detected by a conventional method.

EXAMPLE 2

(1) Reagents and Instrument
PPO Reagent

As a PPO reagent, there was used a solution prepared by dissolving a commercially available PPO reagent derived from silkworm hemolymph (SLP™ reagent, available from Wako Pure Chemical Industries, Ltd.; for 3 ml) in 6 ml of a solvent attached to SLP™ reagent kit (available from Wako Pure Chemical Industries, Ltd.).

Filter

Disposable Sterile Syringe Filters 3 mm (a nylon film, mfd. by Corning Inc.) was used.

Water and Washing Solution

Water for injection mfd. by Otsuka Pharmaceutical Co., Ltd. was used.

Solution After Washing a Hemodialyzer

A hemodialyzer comprising Acetate Hollow Fiber (FB-70A, mfd. by Nipro Corp.) was filled with water for injection and allowed to stand at room temperature for 1 hour, after which the filled water was taken out as a solution after washing the hemodialyzer.

(2) Samples

As samples, there were used suspensions prepared by suspending *E. coli* in water or a solution after washing the hemodialyzer to a density of $10^4$ cells/ml.

(3) Detecting Procedure

The filter was washed with 2 ml of the washing solution and then 0.5 ml of each sample was filtered through the washed filter. This filter was washed with 2 ml of the washing solution, after which 0.01 ml of the PPO reagent was dropped thereon and the degree of coloring of the filter was visually observed.

(4) Results

Figure 3:
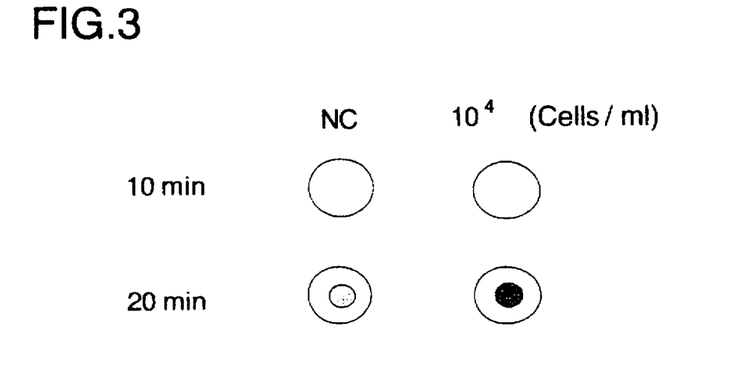
FIG. 3 shows the results of detection of *Escherichia coli* obtained in Example 2.

FIG. 3 shows detection results obtained by using the *E. coli* suspension (prepared by use of water). FIG. 3 also shows results of a negative control test (NC) carried out for comparison by using, as a sample, the same water as used for preparing the above-mentioned sample.

From FIG. 3, it can be seen that the filter having cells retained thereon by the filtration shows clearly rapider coloration than does the filter treated by the negative control test (NC), and makes it possible to judge the existence of *E. coli* at a density of $10^4$ cells/ml and to judge whether the reaction is positive or negative, on 20 minutes after the initiation of the reaction.

When the sample prepared by use of the solution after washing the hemodialyzer was used, the same results as above were obtained.

Comparative Example 2

Detection of microorganisms by a known method
(1) Reagents and instrument
PPO Reagent
The same as used in Example 2.
Water
The same as used in Example 2.
Solution After Washing a Hemodialyzer
The same as used in Example 2.
Measuring Apparatus
Toxinometer ET-301 (mfd. by Wako Pure Chemical Industries, Ltd.) was used.
(2) Samples
The same as used in Example 2.
(3) Detecting Procedure After 0.1 ml of the PPO reagent and 0.1 ml of each sample were mixed and stirred, a Tg value (a time required for the amount of transmitted light to reach a predetermined definite value) was measured by means of Toxinometer ET-301.

(4) Results

When an *E. coli* suspension prepared by use of water was used as a sample, a Tg value of 59.4 minutes was obtained. When the same water as used for preparing the *E. coli* suspension was used as a sample for a negative control, no Tg value could be obtained within a measurement time of 90 minutes. From these facts, it can be seen that in the case of the *E. coli* suspension prepared by use of water, it is possible to judge whether the reaction is positive or negative, within a measurement time of 90 minutes.

On the other hand, a Tg value of about 6 minutes was obtained both when an *E. coli* suspension prepared by use of the solution after washing the hemodialyzer was used as a sample, and when the same solution after washing the hemodialyzer as used for preparing the *E. coli* suspension was used as a sample for a negative control. Thus, it was found that the presence of the microorganism cannot be detected in the sample (the *E. coli* suspension). It can be speculated that this result is due to the dissolution of β-glucan in the solution after washing the hemodialyzer.

From the results of Example 2 and Comparative Example 2, it can be seen that the application of the process of the present invention permits detection of microorganisms in the solution after washing the hemodialyzer which cannot be detected by a conventional method.

EXAMPLE 3

(1) Reagents and Instrument
PPO Reagent
There was used a solution prepared by dissolving a commercially available PPO reagent derived from silkworm hemolymph (SLPTM reagent, available from Wako Pure Chemical Industries, Ltd.; for 3 ml) in 6 ml of a solvent attached to an SLPTM reagent kit (available from Wako Pure Chemical Industries, Ltd.).
Filter
Multiscreen GV filter plate (available from Japan Millipore Ltd.) was used.
Water and Washing Solution
Water for injection mfd. by Otsuka Pharmaceutical Co., Ltd. was used.

(2) Samples
As samples, there were used suspensions prepared by suspending predetermined bacteria in water for injection so as to obtain predetermined concentrations (cells/ml).

(3) Detecting Procedure
Multiscreen GV filter plate washed with 0.2 ml of a washing solution was used for filtering 0.2 ml of a sample. After filtering 0.2 ml of a washing water, a film sheet was adhered to the bottom of the filter plate. Then, 0.1 ml of the PPO reagent was dropped in a well and subjected to measurement of changes in absorbance at 650 nm using a microplate reader (Spectra Max 250, a trade name, mfd. by Molecular Devices Co.) at 30° C. to obtain onset time (a reaction time required to reach the predetermined OD (optical density) value of 0.2 at 650 nm).

Figure 4:
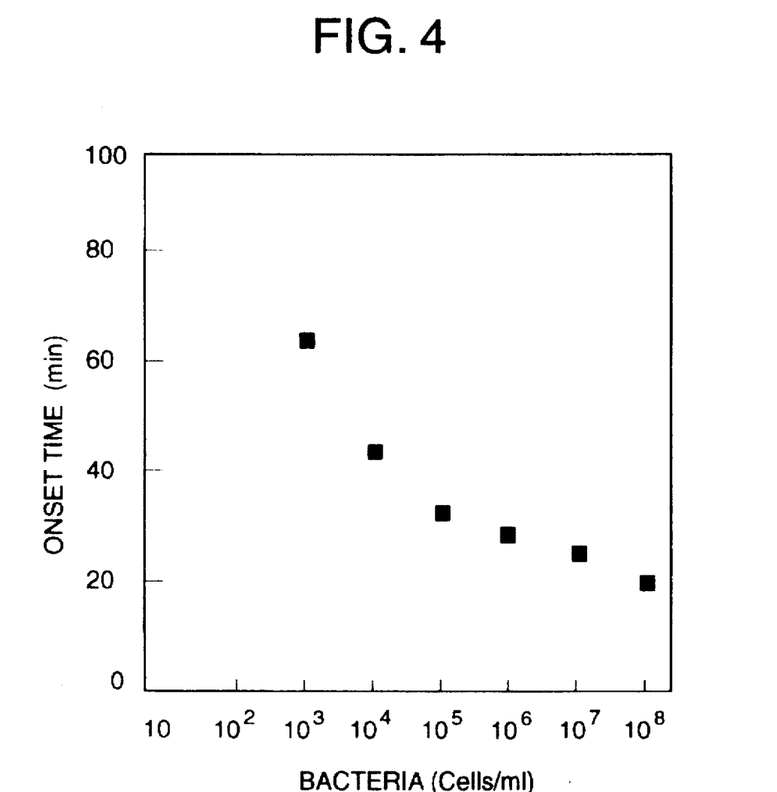
FIG. 4 is a graph showing the results obtained in Example 3 wherein samples contain *Bacillus subtilis*.
Figure 5:
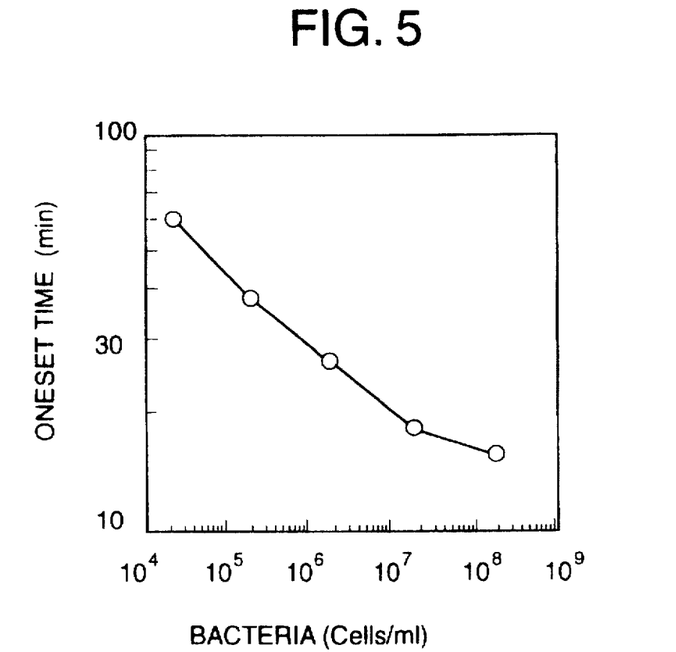
FIG. 5 is a graph showing the results obtained in Example 3 wherein samples contain *Lactobacillus delbrueckii*.
Figure 6:
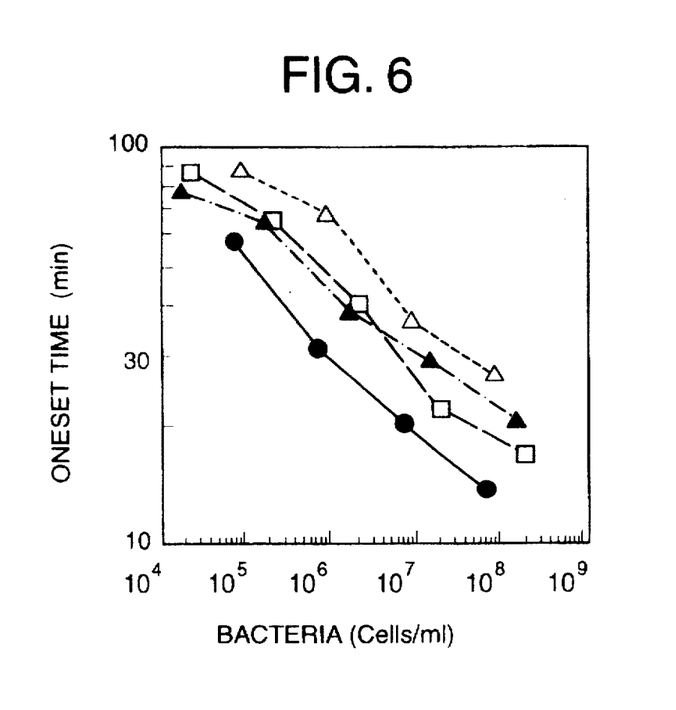
FIG. 6 is a graph showing the results obtained in Example 3 various kinds of bacteria.

(4) Results
FIG. 4 shows the results of samples containing *Bacillus subtilis*. FIG. 5 shows the results of samples containing *Lactobacillus delbrueckii*. FIG. 6 shows the results of samples containing various bacteria.

In FIG. 6, the curve —●— indicates the results of samples containing *Streptococcus mutans* belonging to Gram-positive bacteria, the curve —▲— indicates the results of samples containing *Staphylococcus aureus* belonging to Gram-positive bacteria; the curve —□— indicates the results of samples containing *Aeromonas hydrophila* belonging to Gram-negative bacteria, and the curve —△— indicates the results of samples containing *Vibrio parahaemomolyticus* belonging to Gram-negative bacteria.

As is clear from the results of FIGS. 4 to 6, it is possible to detect concentrations (cells/ml) of various bacteria in samples according to the present invention.

EXAMPLE 4

(1) Reagents and Instrument
PPO Reagent
The same as that used in Example 3.
Filter
The same as that used in Example 3.
Water and Washing Solution
The same as that used in Example 3.

(2) Samples
Samples were prepared by suspending predetermined bacteria in water for injection containing a predetermined concentration of NaCl so as to obtain a predetermined concentration (cells/ml).

(3) Detecting Procedure
Multiscreen GV filter plate washed with 0.2 ml of a washing solution was used for filtering 0.2 ml of a sample. After filtering 0.2 ml of a washing water, a film sheet was adhered to the bottom of the filter plate. Then, 0.1 ml of the PPO reagent was dropped in a well and subjected to measurement of changes in absorbance at 650 nm using a microplate reader (Spectra Max 250, a trade name, mfd. by Molecular Devices Co.) at 30° C. to obtain onset time (a reaction time required to reach the predetermined OD values of 0.2 at 650 nm).

Figure 7:
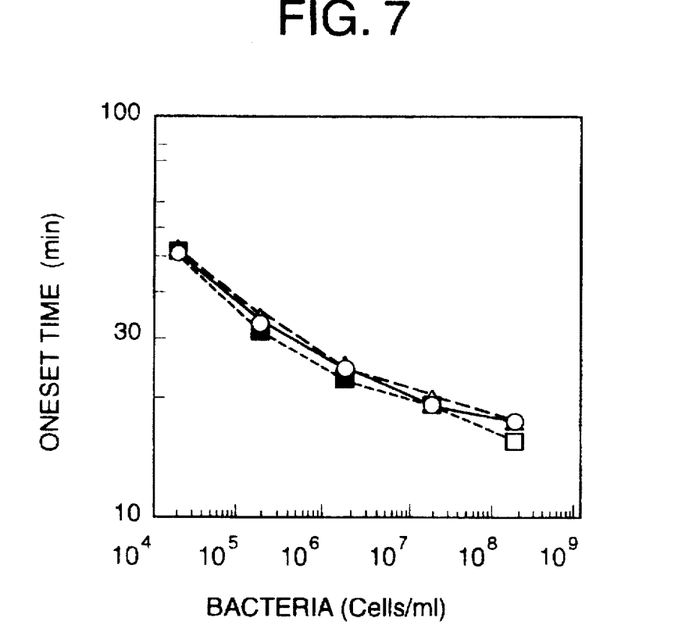
FIG. 7 is a graph showing the results obtained in Example 4.

(4) Results
The results are shown in FIG. 7. In FIG. 7, the curve —○— indicates the results obtained by using samples containing no NaCl, the curve —■— indicates the results obtained by using samples containing 100 mM NaCl, and the curve —△— indicates the results obtained by using samples containing 200 mM NaCl.

Comparative Example 3

Detection of microorganisms by a known method
(1) Reagents and Instrument
PPO Reagent
The same as that used in Example 4.
Water
The same as that used in Example 4.
Microplate
Microplate 96 Well with Lid (3860-096) (mfd. by Iwaki Glass Co., Ltd.) was used.

(2) Samples
Samples were prepared in the same manner as described in Example 4 except for changing concentrations of NaCl.

(3) Detecting Procedure
After mixing 0.1 ml of the PPO reagent and 0.1 ml of a sample, changes in absorbance at 650 nm were measured using a microplate reader (Spectra Max 250, a trade name, mfd. by Molecular Devices Co.) at 30° C. to obtain onset time (a reaction time required to reach the predetermined OD value of 0.2 at 650 nm).

Figure 8:
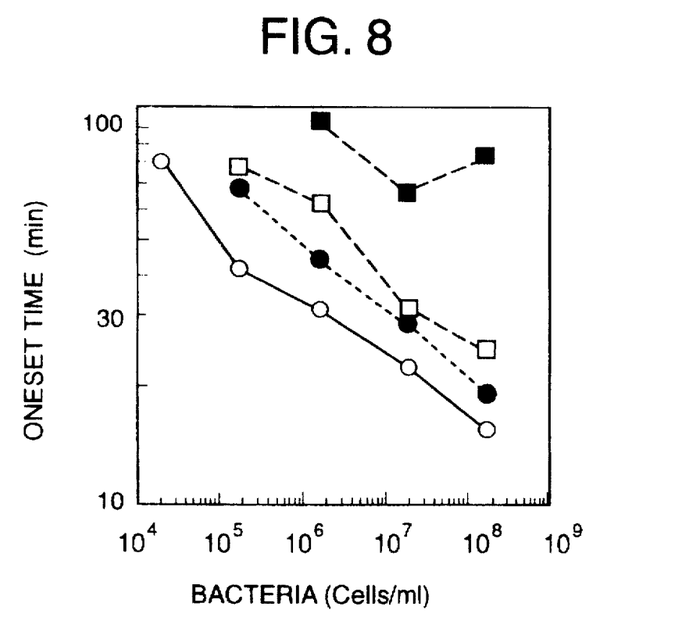
FIG. 8 is a graph showing the results obtained in Comparative Example 3.

(4) Results
The results are shown in FIG. 8. In FIG. 8, the curve —○— indicates the results obtained by using samples containing no NaCl, the curve —●— indicates the results obtained by using samples containing 25 mM NaCl, the curve —□— indicates the results obtained by using samples containing 50 mM NaCl, and the curve —■— indicates the results obtained by using samples containing 100 mM NaCl.

From the comparison of the results shown in FIGS. 7 and 8, it is clear that according to the present invention, it is possible to detect microorganisms in samples containing high salt concentrations in contrast to the known method wherein the detection is impossible.

As described above, the present invention provides a process which permits easy, rapid, and high-precision detection of microorganisms in various samples. The detection of microorganisms in various samples by the detection process of the present invention brings about the marked effects described below which cannot be brought about by a conventional method. Therefore, the present invention contributes greatly to the art.

(1) Microorganisms can be rapidly detected.

The detection can be completed in several hours.

(2) The detection is not affected by substances present in a sample together with microorganisms.

A PPO reagent tends to be influenced by the salt concentration and free β-glucan in the sample, resulting in a lowered measurement sensitivity. But, the process of the present invention can remove this influence because it involves a washing procedure.

(3) Microorganisms in a sample can be concentrated by filtration.

Since the sample is filtered through a filter, the microorganisms in the sample are concentrated, so that the detection sensitivity can be enhanced.

(4) Quantitative determination and qualitative test (limit test) can also be carried out by properly increasing the number of positive controls.

(5) Both viable cells and dead cells can be detected.

(6) Gram-positive bacteria can also be detected.

(7) The detection is not affected by a solvent used for preparing samples.

Even in a case of a specimen soluble only in an organic solvent, an objective detection can be carried out without any influence of the organic solvent by previously carrying out filtration through a filter and washing with a washing solution.

(8) Bacteria or Eumycetes, or both can be measured by changing the kind of a PPO reagent. For example, with the use of a PPO reagent reactive with β-glucan and peptidoglycan, bacteria and Eumycetes can be measured.

With the use of a PPO reagent reactive with β-glucan but not with peptidoglycan, Eumycetes can be measured.

With the use of a PPO reagent reactive with peptidoglycan but not with β-glucan, bacteria can be measured.

(9) Microorganisms to be detected can be chosen by changing the pore size of a filter.

For example, when the detection of bacteria and Eumycetes is desired, a filter having a pore size of 0.2 μm or 0.45 μm is preferable. When the detection of Eumycetes such as yeasts and molds is desired, a filter having a pore size of 1.2 μm to 3 μm is preferable. When the detection of molds is desired, a filter having a pore size of 5 μm or more is preferable. Only bacteria can be detected on a sample containing plural kinds of microorganisms including bacteria, for example, by filtering a sample through a filter having a pore size of 1.2 μm to 3 μm, filtering the filtrate through a filter having a pore size of 0.2 μm or 0.45 μm, and then detecting microorganisms by use of the latter filter.

What is claimed is:

1. A process for detecting microorganisms which comprises filtering a sample containing microorganisms through a filter, washing the filter, reacting the residue on the filter with an insect hemolymph containing inactive factors of the pro-phenol oxidase cascade, and detecting microorganisms in the sample on the basis of the color change.

2. The process according to claim 1, wherein the insect hemolymph is one which reacts with β-glucan but not with peptidoglycan.

3. The process according to claim 1, wherein the insect hemolymph is one which reacts with peptidoglycan but not with β-glucan.

4. The process according to claim 1, wherein the color change is visually observed.

\* \* \* \* \*